United States Patent [19]

Enomoto et al.

[11] Patent Number: 5,041,569

[45] Date of Patent: Aug. 20, 1991

[54] PROCESS FOR PREPARING STYRENE OXIDE

[75] Inventors: Saburo Enomoto; Masami Inoue, both of Toyama; Osami Ohura, Fuji; Tutomu Kamiyama, Toyama; Hirohisa Nitoh, Fuji, all of Japan

[73] Assignee: Tokai Denka Kogyo Kabushiki Kaisha, Tokyo, Japan

[21] Appl. No.: 466,503

[22] Filed: Jan. 17, 1990

[30] Foreign Application Priority Data

Feb. 1, 1989 [JP] Japan .................................. 1-20905

[51] Int. Cl.⁵ ............................................ C07D 301/12
[52] U.S. Cl. .................................... 549/531; 549/529
[58] Field of Search .............................. 549/531, 529

[56] References Cited

U.S. PATENT DOCUMENTS

| | | | |
|---|---|---|---|
| 2,833,787 | 5/1958 | Carlson et al. ...................... | 549/531 |
| 3,806,467 | 4/1974 | Watanabe et al. .................. | 549/531 |
| 3,953,362 | 4/1976 | Lines et al. .......................... | 549/531 |
| 4,157,346 | 6/1979 | Lines et al. .......................... | 549/529 |

OTHER PUBLICATIONS

Abstract of J.P. 55-129276, (1980).
Venturello, et al., J. Org. Chem. 1988, 53, 1553–1557.

*Primary Examiner*—Richard L. Raymond
*Assistant Examiner*—Mark W. Russell
*Attorney, Agent, or Firm*—Scully, Scott, Murphy & Presser

[57] ABSTRACT

Styrene oxide is prepared by reacting styrene and hydrogen peroxide in a heterogeneous system in the presence of a bis(tri-n-alkyltinoxy)molybdic acid and an amine represented by the following general formula:

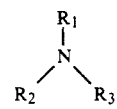

wherein $R_1$, $R_2$ and $R_3$ each independently represent H, $CH_3$, $C_2H_5$, $C_3H_7$, $C_4H_9$, or $HOCH_2CH_2$.

4 Claims, No Drawings

PROCESS FOR PREPARING STYRENE OXIDE

BACKGROUND OF THE INVENTION

The present invention relates to a process for preparing styrene oxide by the reaction of styrene and hydrogen peroxide in the presence of a catalyst.

The application field of styrene oxide covers a wide range; for example, styrene oxide is used as a stabilizer for high polymers, an ultraviolet ray absorber, a starting material of drugs, a stabilizer for solvents, or as a starting material of phenethyl alcohol and phenylaldehyde which are useful as a synthetic perfume and a sweetening material.

For the preparation of styrene oxide, the method of epoxidizing styrene using an organic peracid is most common as is described in Japanese Patent Laid-Open No. 149,271/1980. But this method involves the following drawbacks and is not always satisfactory.

(a) There occurs an addition reaction of a radical to styrene which radical is formed by radical decomposition of an organic peracid during the reaction of oxidizing styrene with the organic peracid, resulting in lowered selectivity of styrene oxide relative to styrene.

(b) An organic acid byproduced after the reaction causes cleavage of the styrene oxide produced, to form an ester and a hydroxy compound, resulting in that the selectivity of styrene oxide relative to styrene is lowered.

(c) Peracetic acid which is most easily available industrially among organic peracids is prepared by a so-called Daicel-Wacker process involving air oxidation of acetaldehyde. But it is a very expensive oxidizing agent.

(d) Close attention must be paid to operation and apparatus in order to avoid the risk involved in the use of an organic peracid.

On the other hand, in the oxidation reaction using hydrogen peroxide, the by-product is only water and there arises no problem related to evironmental pollution; besides, hydrogen peroxide is easily available industrially and inexpensive, so in principle hydrogen peroxide is a desirable epoxidizing agent. However, in the reaction of styrene and hydrogen peroxide to form an epoxide, both the conversion of styrene and the selectivity to epoxide are low. The reason why the conversion is low is that in a low-temperature reaction hydrogen peroxide remains unreacted, while in a high-temperature reaction it decomposes to produce oxygen, and thus hydrogen peroxide is not effectively consumed in the reaction.

The reason why selectivity to epoxide is low is that a polyol is formed by the water which is introduced into the reaction system together with hydrogen peroxide and also by the water which is produced by the reaction.

The reactivity in epoxidation of styrene is as shown in the following table [see "Encyclopedia of Polymer Science and Technology," Vol. VI, Interscience Publishers, N.Y. (1967), p. 83]. It is seen from this table that the relative reactivity in epoxidation of styrene is slower than that of other olefins, for example, about one-tenth of the relative reactivity in epoxidation of cyclohexene, thus indicating a very slot epoxidation reaction of styrene.

| Olefin | Relative Reactivity |
| --- | --- |
| $CH_2=CH_2$ | 1 |
| $C_6H_5CH_2-CH=CH_2$ | 11 |
| $R-CH=CH_2$ | 25 |
| $Ar-CH=CH-Ar$ | 27 |
| $Ar-CH=CH_2$ | 60 |
| $Ar-CH=CH-R$ | 240 |
| $(Ar)_2C=CH_2$ | 250 |
| $R-CH=CH-R$ | 500 |
| $(R)_2C=CH_2$ | 500 |
| cyclohexene | 675 |
| cycloheptene | 900 |
| cyclopentene | 1000 |
| $(R)_2C=CH-R$ | 6500 |
| $(R)_2C=C(R)_2$ | >>6500 |

In the above table, Ar and R represent aryl and alkyl, respectively.

Heretofore, in the preparation of styrene oxide by the reaction of styrene and hydrogen peroxide, there has been proposed the use of a specific catalyst for solving the above-mentioned problems. For example, C. Bentoureluro et al. (J. Org. Chem., 53, 1553, 1988) reports that styrene oxide is obtained in 74% yield (based on hydrogen peroxide) by using a quaternary ammonium salt of phosphotungstic acid as a hydrogen peroxide epoxidizing catalyst. Although this method affords a greatly improved yield as compared with other conventional methods, it is difficult to adopt this method industrially because the quaternary ammonium salt (interphase transfer catalyst) used as a catalyst component is very expensive.

In Japanese Patent Laid-Open No. 129,276/1980 there is proposed a method of reacting styrene and hydrogen peroxide in the presence of arsenic oxide and a 3,5-di-tert-butyl-4-hydroxytoluene. However, this method is disadvantageous in that when arsenic oxide is used together with aqueous hydrogen peroxide, the hydrogen peroxide will decompose rapidly, or the epoxidizing speed is uneconomical. Further, since arsenic compounds are highly toxic, it is necessary to exercise ample care about the manufacturing equipment in order to prevent the workers or users from being poisoned during manufacture or at the time of use due to incorporation of an arsenic compound in the product.

U.S. Pat. No. 3,806,467 proposes a process for preparing an epoxide by the reaction of an olefin and hydrogen peroxide in the presence of a bis(tri-n-methyltinoxy)molybdic acid catalyst. According to the working examples thereof, the yield of cyclohexene epoxide is high and the process is an effective process, but the yield of styrene oxide is a little less than 3% (based on hydrogen peroxide) and thus it cannot be said that the process is a preferable process for the preparation of styrene oxide. The reason for such a poor yield of styrene oxide is presumed to be because of oxidative cleavage of the styrene oxide produced, resulting in by-production of benzaldehyde and benzoic acid.

SUMMARY OF THE INVENTION

It is an object of the present invention to overcome the above-mentioned drawbacks of the conventional processes.

The bis(tri-n-alkyltinoxy)molybdic acid catalyst described in the foregoing U.S. Pat. No. 3,806,467 is industrially inexpensive and easily available and can be immobilized to active carbon and organic matter adsorbing resins, thus permitting the reaction system to be a heterogeneous catalyst system, whereby the catalyst can be easily separated from the reaction system.

It is another object of the present invention to provide a promotor which exhibits an outstanding effect in combination with the said catalyst.

The present invention resides in a process for preparing styrene oxide by the reaction of styrene and hydrogen peroxide in the presence of a bis(tri-n-alkyltinoxy)-molybdic acid catalyst, wherein an amine having the following structural formula is also made present as a promotor and the reaction is carried out in an heterogeous system:

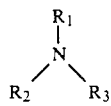

where $R_1$, $R_2$ and $R_3$ each independently represent H, $CH_3$ $C_2H_5$, $C_3H_7$, $C_4H_9$, or $HOCH_2CH_2$.

By the process of the present invention it is possible to obtain the desired styrene oxide in high activity at a low temperature, in high yield and high selectivity.

DETAILED DESCRIPTION OF THE INVENTION

The hydrogen peroxide used in the present invention may be a commonly-used one. There may be used an aqueous solution thereof having a concentration of 5% to 90%, but it is desirable to use an aqueous solution thereof having a concentration of 10° C. to 70% which is available easily.

In the reaction of styrene and hydrogen peroxide, the ratio of the two may be an equimolar ratio, but either one material may be used in a too small or too large amount. For example, usually 0.1 to 3.0 moles of hydrogen peroxide may be used per mole of styrene, but preferably the former is used in an amount of 0.3 to 2.0 moles.

The bis(tri-n-alkyltinoxy)molybdic acid catalyst used in the present invention can be prepared easily by known method. But, molybdenum blue and a tri-n-alkyltin oxide, which are the components of the catalyst, may be added separately to the reaction system to prepare the catalyst. As examples of tri-n-alkyltin oxides employable in the present invention there are mentioned tri-n-methyltin oxide, tri-n-ethyltin oxide, tri-n-propyltin oxide and tri-n-butyltin oxide.

As to the amount of the catalyst to be used, the lower limit thereof is usually not less than 0.0001 mole, preferably not less than 0.001 mole, and the upper limit thereof is usually not more than 0.1 mole, preferably not more than 0.01 mole, per mole of styrene.

The amine used as a promotor has the following structure formula:

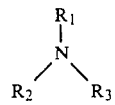

wherein $R_1$ $R_2$ and $R_3$ each independently represent H, $CH_3$, $C_2H_5$, $C_3H_7$, $C_4H_9$, or $HOCH_2CH_2$. Examples of such amine include ammonia, primary, secondary and tertiary methylamines, primary, secondary and tertiary ethylamines, primary, secondary and tertiary n-propylamines, primary, secondary and tertiary iso-propylamines, primary, secondary and tertiary butylamines, primary, secondary and tertiary ethanolamines.

The amount of the amine used as a promotor is in the range of 0.1 to 2.0 moles per mole of the bis(tri-n-alkyltinoxy)molybdic acid catalyst, preferably an equimolar amount.

The epoxidation reaction in the present inventions is conducted in a heterogeneous system. The heterogeneous system is formed by using an organic solvent which is immiscible with water. More particularly, the starting styrene and the oxidation product, styrene oxide, are present in a dissolved state in an organic solvent immiscible with water, while hydrogen peroxide is present in an aqueous phase, and thus there are formed two phases which are the organic solvent phase and the aqueous phase. By using a water-immiscible organic solvent, it is possible to avoid contact of the oxidation product, styrene oxide, with water and hydrolysis.

The organic solvent used in the present invention is not specially limited if only it is inert to the reaction and immiscible with water. Examples are dichloromethane, chloroform, carbon tetrachloride, dichloroethane, trichloroethane, tetrachloroethane, dichloroethylene, trichloroethylene, tetrachloroethylene, monoclorobenzene, dichlorobenzene, benzene, toluene, xylene and mesitylene.

The reaction can be performed at a relatively low temperature because the catalyst used in the present invention is very active as compared with conventional catalysts. The reaction temperature is usually in the range of 0° C. to 100° C., preferably 10° C. to 70° C.

The following examples are given to illustrate the present invention in more detail, but it is to be understood that the invention is not limited thereto.

EXAMPLE-1

43.8 mmol of styrene, 5 ml of chloroform, 0.35 mmol of tri-n-butyltin oxide, about 0.35 mmol of molybdenum blue and 0.35 mmol of 30% trimethylamine were charge into an Erlenmeyer flask having a capacity 50 ml, and stirring was made at room temperature for 20 minutes. After dissolution of the tri-n-butyltin oxide and molybdenum blue, 21.9 mmol of 60% hydrogen peroxide was added at a time and reaction was allowed to take place for 24 hours in a shaking type constant temperature bath held at 25° C.

Analysis was made for styrene and styrene oxide by gas chromatography, while the residual amount of hydrogen peroxide was determined by an iodo titration method. The results are as shown in Table 1.

EXAMPLE-2

Reaction was carried out in the same way as in Example-1 except that reaction time was changed to 7 hours. The results are as shown in Table 1.

EXAMPLE-3

Reaction was carried out in the same way as in Example-1 except that 0.35 mmol of bis(tri-n-butyltinoxy)-molybdic acid was used in place of the tri-n-butyltin oxide and molybdenum blue. The results are as shown in Table 1.

COMPARATIVE EXAMPLE-1

Reaction was carried out in the same way as in Example-1 except that trimethylamine was not used. The results are as shown in Table 1.

TABLE 1

| | (based on hydrogen peroxide) | | |
|---|---|---|---|
| | Conversion | Yield | Selectivity |
| Comp. Example 1 | 87% | 10% | 12% |
| Example 1 | 96% | 82% | 86% |
| Example 2 | 90% | 81% | 90% |
| Example 3 | 96% | 77% | 81% |

EXAMPLE-4

8.7 mmol of styrene, 5 ml of chloroform, 0.35 mmol of tri-nobutyltin oxide, about 0.35 mmol of molybdenum blue and 0.35 mmol of 30% trimethylamine were charged into an Erlenmeyer flask having a capacity of 50 ml, and stirring was made at room temperature for 20 minutes. After dissolution of the tri-n-butyltin oxide and molybdenum blue, 21.9 mmol of 60% hydrogen peroxide was added at a time and reaction was allowed to take place for 7 hours in a shaking type constant temperature bath held at 25° C. The results are as shown in Table 2.

EXAMPLE-5

Reaction was carried out in the same way as in Example-4 except that 0.35 mmol of dimethylamine was used in place of the trimethylamine. The results are as shown in Table 2.

EXAMPLE-6

Reaction was carried out in the same way as in Example-4 except that 0.35 mmol of monomethylamine was used in place of the trimethylamine. The results are as shown in Table 2.

EXAMPLE-7

Reaction was conducted in the same way as in Example-4 except that 0.35 mol of ammonia was used in place of the trimethylamine. The results are as forth Table 2.

EXAMPLE-8

Reaction was conducted in the same manner as in Example-4 except that 0.35 mmol of triethylamine was used in place of the trimethylamine. The results are as set forth in Table 2.

EXAMPLE-9

Reaction was conducted in the same manner as in Example-4 except that 0.35 mmol of triisopropylamine was used in place of the trimethylamine. The results are as set forth in Table 2.

EXAMPLE-10

Reaction was conducted in the same manner as in Example-4 except that 0.35 mmol of tributylamine was used in place of the trimethylamine. The results are as set forth in Table 2.

EXAMPLE-11

Reaction was conducted in the same manner as in Example-4 except that 0.35 mmol of triethanolamine was used in place of the trimethylamine. The results are as set forth in Table.

COMPARATIVE EXAMPLE-2

Reaction was performed in the same manner as in Example-4 except that the trimethylamine was not used. The results are as set forth in Table 2.

TABLE 2

| | (based on styrene) | | |
|---|---|---|---|
| | Conversion | Yield | Selectivity |
| Comp. Example 2 | 85% | 4% | 5% |
| Example 4 | 78% | 73% | 94% |
| Example 5 | 66% | 60% | 91% |
| Example 6 | 81% | 68% | 84% |
| Example 7 | 68% | 64% | 93% |
| Example 8 | 76% | 66% | 87% |
| Example 9 | 66% | 77% | 89% |
| Example 10 | 57% | 55% | 97% |
| Example 11 | 60% | 58% | 97% |

EXAMPLE-12

8.7 mmol of styrene, 5 ml of chloroform, 0.70 mmol of tri-n-butyltin oxide, about 0.35 mmol of molybdenum blue and 0.14 mmol of 30% trimethylamine were charged into an Erlenmeyer flask having a capacity of 50 ml, and stirring was made at room temperature for 20 minutes. After dissolution of the tri-n-butyltin oxide and molybdenum blue, 21.9 mmol of 60% hydrogen peroxide was added at a time and reaction was allowed to take place for 5 hours in a shaking type constant temperature bath held at 25° C. The results are as set forth in Table 3.

EXAMPLE-13

Reaction was performed in the same manner as in Example-12 except that the amount of the trimethylamine used was changed to 0.21 mmol. The results are as set out in Table 3.

EXAMPLE-14

Reaction was performed in the same manner as in Example-12 except that the amount of the trimethylamine used was changed to 0.39 mmol. The results are as set out in Table 3.

EXAMPLE-15

Reaction was performed in the same manner as in Example-12 except that the amount of the trimethylamine used was changed to 0.70 mmol. The results are as set out in Table 3.

EXAMPLE-16

Reactions was performed in the same way as in Example-15 except that the reaction time was changed to 10 hours. The results are as set out in Table 3.

TABLE 3

| | (based on styrene) | | |
|---|---|---|---|
| | Conversion | Yield | Selectivity |
| Comp. Example 12 | 82% | 67% | 82% |
| Example 13 | 68% | 64% | 93% |
| Example 14 | 55% | 54% | 97% |
| Example 15 | 7% | 7% | 100% |
| Example 16 | 39% | 38% | 97% |

EXAMPLE-17

14.6 mmol of styrene, 5 ml of chloroform, 0.35 mmol of tri-n-butyltin oxide, about 0.35 mmol of molybdenum blue and 0.35 mmol of 30% trimethylamine were charged into an Erlenmeyer flask having a capacity of 50 ml, and stirring was made at room temperature for 20 minutes. After dissolution of the tri-n-butyltin oxide and molybdenum blue, 21.9 mmol of 60% hydrogen peroxide was added at a time and reaction was allowed to take place for 7 hours in a shaking type constant temperature bath held at 25° C. The results are as shown in Table 4.

EXAMPLE-18

Reaction was performed in the same way as in Example-17 except that 5 ml of dichloroethane was used in place of the chloroform. The results are as shown in Table 4.

EXAMPLE-19

Reaction was performed in the same way as in Example-17 except that 5 ml of benzene was used in place of the chloroform. The results are as shown in Table 4.

COMPARATIVE EXAMPLE-3

Reaction was performed in the same way as in Example-17 except that 5 ml of acetonitrile was used in place of the chloroform. The results are as shown in Table 4.

COMPARATIVE EXAMPLE-4

Reaction was carried out in the same way as in Example-17 except that 5 ml of t-butyl alcohol was used in place of the chloroform. The results are as shown in Table 4.

TABLE 4

| | (based on styrene) | | |
|---|---|---|---|
| | Conversion | Yield | Selectivity |
| Comp. Example 3 | 32% | 15% | 48% |
| Comp. Example 4 | 56% | 31% | 56% |
| Example 17 | 68% | 64% | 93% |
| Example 18 | 54% | 45% | 83% |
| Example 19 | 41% | 38% | 93% |

What is claimed is:

1. A process for preparing styrene oxide which comprises reacting styrene and hydrogen peroxide in a heterogeneous system in the presence of a abis(tri-n-alkyl-tinoxy)molybdic acid and an amine represented by the following general formula:

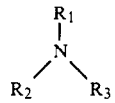

wherein $R_1$, $R_2$ and $R_3$ each independently represent H, $CH_3$, $C_2H_5$, $C_3H_7$, $C_4H_9$, or $HOCH_2CH_2$ where said heterogeneous system comprises water and an organic solvent immisible with water, said styrene and styrene oxide being soluble in said solvent.

2. A process as set forth in claim 1, wherein the amount of said bis(tri-n-alkyltinoxy)molybdic acid used is in the range of 0.001 to 0.1 mole per mole of styrene.

3. A process as set forth in claim 1, wherein the amount of said amine used is in the range of 0.1 to 2.0 moles per mole of said bis(tri-n-alkyltinoxy)molybdic acid.

4. A process as set forth in claim 1, wherein the reaction is carried out at a temperature in the range of °C. to 100° C.

* * * * *